(12) United States Patent
Piccinini et al.

(10) Patent No.: US 11,666,230 B1
(45) Date of Patent: Jun. 6, 2023

(54) ELECTRONIC DEVICE AND METHOD FOR NONINVASIVE, CONTINUOUS BLOOD PRESSURE MONITORING

(71) Applicants: Jose Maria Piccinini, Buenos Aires (AR); Eliana Aversa, Buenos Aires (AR); Graciela Aurora Ruiz, Buenos Aires (AR); Raul Chirife, Buenos Aires (AR)

(72) Inventors: Jose Maria Piccinini, Buenos Aires (AR); Eliana Aversa, Buenos Aires (AR); Graciela Aurora Ruiz, Buenos Aires (AR); Raul Chirife, Buenos Aires (AR)

( * ) Notice: Subject to any disclaimer, the term of this patent is extended or adjusted under 35 U.S.C. 154(b) by 0 days.

(21) Appl. No.: 17/814,866

(22) Filed: Jul. 26, 2022

(51) Int. Cl.
 A61B 5/021 (2006.01)
 A61B 5/024 (2006.01)

(52) U.S. Cl.
 CPC .......... *A61B 5/021* (2013.01); *A61B 5/02416* (2013.01); *A61B 5/02108* (2013.01)

(58) Field of Classification Search
 CPC .. A61B 5/021; A61B 5/02416; A61B 5/02108
 See application file for complete search history.

(56) References Cited

U.S. PATENT DOCUMENTS

| | | |
|---|---|---|
| 10,159,441 B2 | 12/2018 | Narasimhan |
| 10,702,169 B2 | 7/2020 | Gaurav |
| 2011/0288421 A1 | 11/2011 | Banet |
| 2018/0070833 A1* | 3/2018 | Chirife .............. A61B 5/686 |

FOREIGN PATENT DOCUMENTS

WO  WO20200157114  8/2020

OTHER PUBLICATIONS

M. Das, T. Choudhary, L. N. Sharma and M. K. Bhuyan, "Noninvasive Accelerometric Approach for Cuffless Continuous Blood Pressure Measurement," in IEEE Transactions on Instrumentation and Measurement, vol. 70, pp. 1-9, 2021 (Year: 2021).*

* cited by examiner

*Primary Examiner* — Christian Jang
*Assistant Examiner* — Mitchell E Alter
(74) *Attorney, Agent, or Firm* — Defillo & Associates, Inc.; Evelyn A. Defillo

(57) ABSTRACT

An electronic device and method for continuous noninvasive blood pressure monitoring in a subject having an electronic device capable of receiving, storing and processing data from an arterial pulse waveform sensor. The electronic device detects key landmarks on the arterial pulse waveform allowing the calculation of pulse rate and left ventricular ejection time (LVET). Based on experimentally determined regression equations between rate-corrected LVET and systolic diastolic and pulse blood pressures, prevailing beat-to-beat blood pressure values are calculated. The only input required for continuous blood pressure monitoring is an arterial pulse waveform, detected in the present invention by a single sensor device, for example a photoplethysmography pulse detector. An electronic device suitable for performing this noninvasive method is further provided.

5 Claims, 3 Drawing Sheets

ELECTRONIC DEVICE AND METHOD FOR NONINVASIVE, CONTINUOUS BLOOD PRESSURE MONITORING

TECHNICAL FIELD

This invention relates generally to the field of noninvasive medical diagnostic devices and more particularly to a noninvasive, beat-to-beat, continuous, cuff-less blood pressure monitoring, applicable to stationary, portable or implantable medical diagnostic systems as well as in wearable devices such as smart watches.

BACKGROUND OF THE INVENTION

Arterial blood pressure (BP) is an important physiological parameter. The health and proper perfusion of the body organs and systems depend on it. BP varies when adapting to external or internal physiological challenges, but pathological variations may lead to a deterioration of various organs[1].

Hypertension is a pathological condition characterized by predominantly increased BP that exceeds what is considered a normal range. High BP forces the heart to work harder to pump blood throughout the arterial system, leading to thickening of heart wall and hardening of the arteries, both increasing risk of damage to various organs such as the heart, kidney, brain and other organs. Many of these damages can occur before the patient manifests any symptom. For this reason, hypertension is frequently referred to as the "silent killer".

It has been shown in numerous studies that lowering BP reduces risk of above disabling conditions, and frequent controls are essentials to guide the proper treatment.

Hypotension refers to a reduction of BP below normal values. Although this condition is not as severe as hypertension, it can also cause problems, such as cognitive impairment and transient loss of consciousness (syncope). Paradoxically, many patients who have arterial hypertension may have episodes of hypotension when changing their body position or after food intake. Since such patients are occasionally treated with antihypertensive drugs, a close monitoring of BP is needed to prevent and treat an excessive blood pressure drop.

In view of above, different methods were developed for automatic blood pressure monitoring. These include the traditional auscultatory Korotkoff method, using an arm cuff connected to a pressure manometer, which automatically inflates and deflates periodically, and a microphone to detect arterial sounds. Upon cuff deflation the value of cuff pressure at the time of detection of the first arterial sound indicates systolic pressure, while the cuff pressure at the time of disappearing of arterial sounds, indicates the value of diastolic blood pressure. Similarly, other devices using the intermittent cuff inflation method for BP monitoring, use the arterial oscillations as markers of systolic and diastolic pressures (Pachon oscillometer method). Although these methods are used for blood pressure monitoring, they are imprecise and uncomfortable for the patient, especially at night. Intermittent BP monitoring with the cuff method applied to the wrist is also feasible, but it is required that the wrist bracelet either be placed at heart level or a hydrostatic compensation mechanism be used. These cuff-based methods may be adequate for overall assessment of hypertension or hypotension, but they are not always adequate. For example, in patients with syncope, the timing of BP measurement may not coincide with the patient's symptoms, such as chest pain or temporary loss of consciousness.

Examples are U.S. Pat. No. 10,159,441; US20110288421; U.S. Ser. No. 10/702,169; and WO20200157114.

An additional inconvenience is that blood pressure measurements take over 30 to 40 seconds to be completed. In such cases, it would be more useful to have a continuous, beat-to-beat assessment of blood pressure.

Several methods for continuous cuff-less non-invasive blood pressure monitoring using surrogates of changes in blood pressure from baseline values have been proposed, but all proposed devices require the recording of more than one channel, namely one pulse and the ECG or two arterial pulse waves, obtained with photoplethysmogram, cardiac accelerometer tissue impedance or cardiac seismogram with a simultaneous reference electrocardiogram channel. Examples include the measurement of Pulse Transit Time (PTT) or Pulse Arrival Time (PAT). For the PTT, two different signals are required: an ECG and a pulse signal. The PTT is the time elapsed between the R-wave (onset) of the ECG and the foot or peak of a detected arterial pulse waveform. This method uses the time between the ECG and the onset of the pulse wave, incorrectly referred to as "pulse wave transit time" as a surrogate for changes in basal blood pressure. Such denomination is erroneous because the measurement represents the sum of two intervals with opposite hemodynamic implications: the pre-ejection period (PEP), that is, time between the QRS and the onset of ventricular ejection at the central level, plus the true pulse transit time, which does have an inverse relationship with systolic blood pressure). It has been observed that when arterial pressure increases, the PEP lengthens and the true PTT shortens, which would explain the low diagnostic value of this method using only the time between the QRS and the onset of a peripheral pulse. The PAT method uses two pulse signals obtained from two different points of the same or different arteries.

The pulse arrival (or propagation) time between the two arterial sensors is measured. Its operation is based on the fact that the higher the blood pressure, the higher the stiffness in the artery, causing the pressure waveform to propagate at a higher velocity, shortening transit time. These methods (PAT and PTT) need the combination of two signals: an electrocardiogram plus a pulse wave, or two different pulse waves.

Because of the above limitations continuous BP measurements with a small, reliable and portable device using PAT or PTT have not been reliably implemented.

Single Sensor for Continuous, Blood Pressure Monitoring

An accurate way to measure BP is by using a pressure transducer placed through an artery, with the pressure sensor near the aortic valve, that is, close to the heart. Although the method is accurate and it allows for a beat-to-beat quantification, it is invasive and hence not applicable in the ambulatory clinical practice. Continuous beat-to-beat blood pressure can be accomplished only for limited periods using Peñaz's method in which a servomechanism produces an external pressure on a finger photoplethysmography sensor. The pressure generated by the servomechanism is indicative of the finger arterial blood pressure. Although this method is accurate, it is also very complex, non-portable, affected by arm position and requires frequent calibration.

SUMMARY OF THE INVENTION

Changes of rate-corrected left ventricular ejection time (LVETc) as surrogates of blood pressure changes In the present invention the inventors describe a novel, simple device and method for continuous blood pressure tracking using a single input to the device. It is based on the behavior of so-called systolic time intervals, which have been studied for decades, as markers of cardiac function. Traditionally, the cardiac cycle is divided into systole and diastole, the former being related to forward cardiac pump function, that is, to the general circulation, and the latter related to ventricular filling. Said mechanical events are preceded by electrical depolarization of the heart muscle, referred to as ECG. In order to assess systolic cardiac function, systolic time intervals (STI) have been used for decades. The time elapsed between the beginning of electrical depolarization (ECG) and the end of ventricular ejection is known as electromechanical systole, which has two intervals: the first one is the pre-ejection period (PEP), extending from the beginning of the ECG to the beginning of left ventricular ejection, which is when the aortic valve opens. The second interval is the left ventricular ejection, generally referred to as left ventricular ejection time (LVET).

Of note, LVET is a timing event reflecting central cardiac phenomenon, unlike pulse amplitude measurements that are determined by the detection site. It has been shown, for example, that LVET measured from peripheral arteries with a photoplethysmogram is the same as that measured with an intra-arterial catheter placed in the central aorta, close to the heart. Furthermore, LVET measured from a finger photoplethysmogram was shown to be the same as that from the external carotid artery. LVET is a timing event extending from the onset of ventricular ejection, signaled by the upstroke of a peripheral or central pulse wave, to the end of ejection, signaled by the dicrotic notch, a marker of aortic valve closure. Therefore, this interval can be measured using a single pulse signal anywhere an arterial pulse is detected. FIG. 1 shows how LVET and cycle length (CL) can be obtained from a pulse signal. LVET is influenced by heart rate, cardiac preload (blood returning to heart), ventricular contractility (muscle contraction force) and ventricular afterload (pressure in aorta, when aortic valve opens). It is well known that LVET is strongly associated with heart rate, stroke volume, and blood pressure. To offset the influence of heart rate, LVET should be rate-corrected or normalized (LVETc) using published regression equations.

Said regressions are obtained from the association between heart rate and LVET. An example of this is Weissler's formula which corrects LVET for a hypothetical heart rate of zero. Normalization of LVET for other heart rates, such as to 60 bpm as done in the present invention, is also suitable. Adjusting LVET for cycle length is also possible, but the resulting relationship is non-linear.

When a patient changes from supine to standing position, a momentary BP decrease occurs because of preload reduction (venous blood pooling in legs), and HR increases as a physiologic compensatory mechanism. Under said conditions, LVETc shortens.

The inventors have observed such changes in a group of 196 patients who underwent a diagnostic head-up tilt test (orthostatic test on a tilt table). Shortening of LVET associated with drop in BP suggested that LVET changes may behave as a surrogates of blood pressure changes.

To further validate the assumption that LVETc changes may parallel changes in BP, the inventors evaluated 30 additional patients. In this study, patients had a previously implanted dual-chamber cardiac pacemaker, allowing the timing between atrial contraction and ventricular contraction, known as atrio-ventricular (AV) interval, to be modulated using a conventional pacemaker programmer. Changing AV interval changes left ventricular end-diastolic volume, known as cardiac preload. Such AV interval modulation leads to changes in the ventricular preload, that is, heart blood volume just before ejection. Said preload changes cause changes in arterial blood pressure. In each patient, the inventors measured beat-to-beat arterial blood pressure with a calibrated FINAPRES™ device. At least 20 beats with a normal AV interval and 20 beats with a short AV were recorded. Systolic blood pressure dropped 11% when shifting from a normal AV to a short AV and LVETc dropped 9%. Furthermore, the inventors observed that BP and LVETc changed in the same direction when BP was modulated by changing preload (namely AV interval) by cardiac pacing. This simple experiment allowed the inventors to test the hypothesis that changes in blood pressure parallel changes of LVETc. Having obtained the regression equations for the correlations between systolic, diastolic and pulse pressure changes and LVETc in the group of 30 patients, the inventors then tested how said regression equations would predict blood pressure changes in the individual patient. For an easier understanding, the blood pressure (B) will hereinafter generally refer to systolic, diastolic, and pulse pressures.

In summary, it was established that a strong association exists between measured LVETc changes and actual blood pressure changes, using as a reference a calibrated noninvasive beat-to-beat blood pressure recording apparatus (FINAPRES™)

BRIEF DESCRIPTION OF THE DRAWINGS

The following drawings and the associated descriptions are provided to illustrate embodiments of the present disclosure and should not be taken as a limitation.

DETAILED DESCRIPTION OF THE INVENTION

One of several possible embodiments of the present invention is hereby detailed for anyone expert in the art to understand. According to studies carried out by the inventors, and based on physiological recordings, it was concluded that changes in systolic and diastolic blood pressures are strongly associated with changes of rate-corrected left ventricular ejection time (LVETc).

Based on above observation and statistical work, the inventors obtained regression equations allowing prediction of arterial blood pressure variations from a baseline value by the simple measurement of LVETc variations. In the foregoing example the basic steps needed for prediction of BP changes from LVETc changes, referenced to baseline calibration blood pressures. For example, if calibration systolic blood pressure is 150 mmHg, and calculations indicate that, based on LVETc changes, systolic blood pressure should change by 10%, then the predicted systolic blood pressure would be 150+15=165 mm Hg. The following description makes reference to block diagram in FIG. 3.

According to the disclosure, the device (318) should have capability to collect, store and process information.

Figure 1:
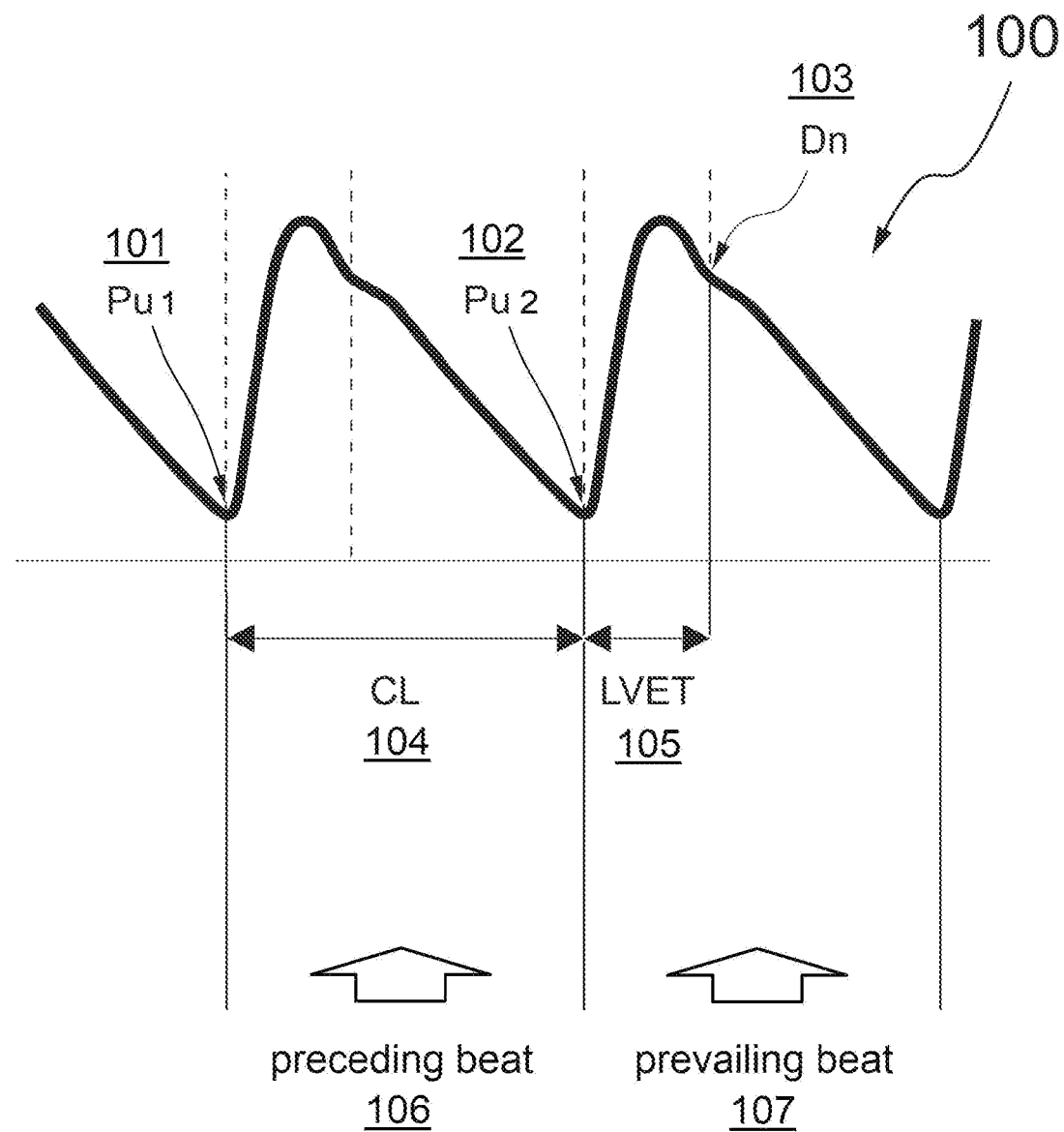
FIG. 1 is an example graph of arterial pulse waveform such as that obtained from a photoplethysmography. It shows two particularly important time landmarks for the purpose of the present invention: beat-to-beat cycle length (CL) and left ventricular ejection time (LVET). CL is measured from the pulse upstroke of the preceding beat (Pu1) to the upstroke of the prevailing beat (Pu2). LVET comprises the time between Pu2 and the pulse wave dicrotic notch (Dn). Said measurement landmarks can be enhanced with digital filtering to increase measurement precision.
Figure 2:
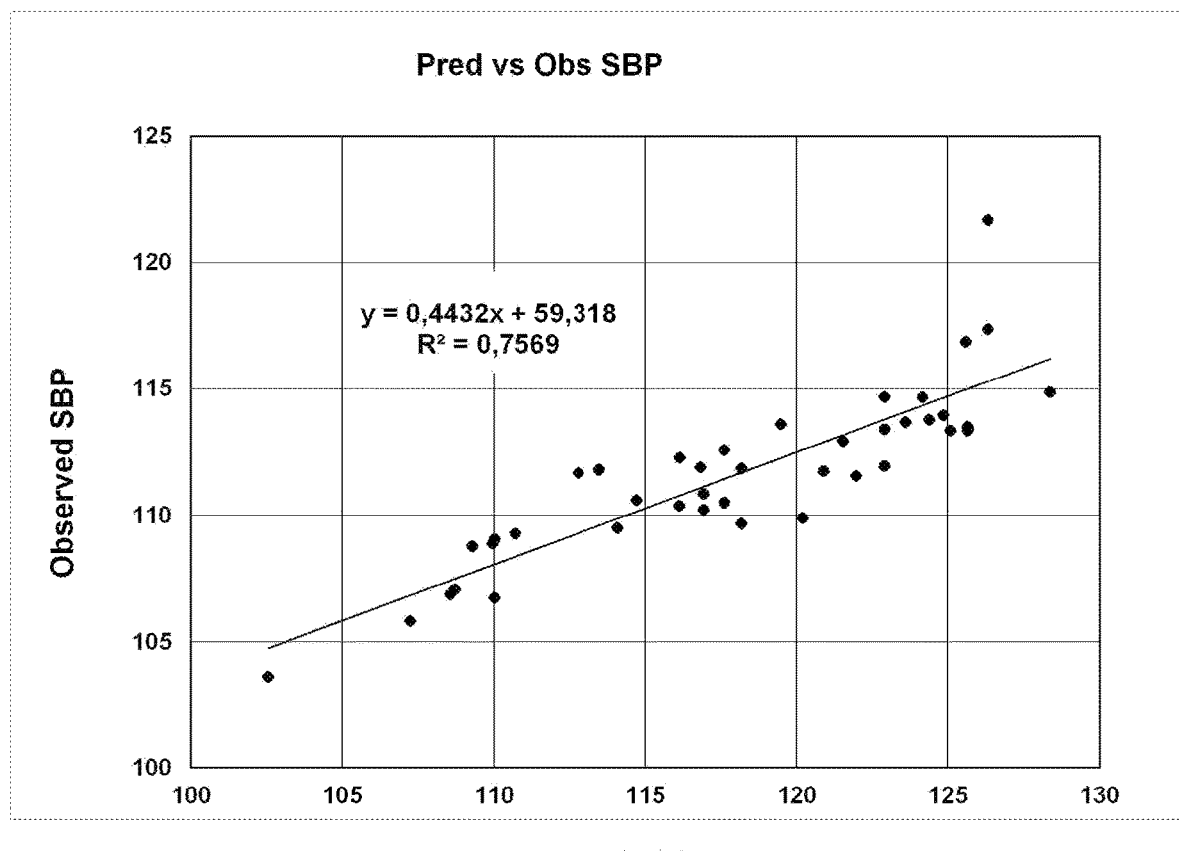
FIG. 2 is a graph showing the highly significant correlation between predicted (x-axis) vs. measured (y-axis) systolic blood pressures in an example subject in whom blood pressure changes were calculated from percentage changes of LVETc, as described in this invention.

For LVET measurements the arterial pulse waveform (100) obtained in foregoing example from a photoplethysmography (31) is amplified (32) digitally sampled and filtered (33) to enhance landmarks shown in FIG. 1, namely the upstroke (101 and 102), detected in block 35, and the dicrotic notch (103), detected in block 36, from arterial pulse waveform (100). Three distinct waveform landmarks are required for rate-corrected LVETc measurement: the foot of the pulse upstroke of the preceding beat, Up1 (101), the pulse upstroke of the prevailing beat, Up2 (102), and the dicrotic notch Dn (103) of the prevailing beat (107). The timing between Up1 (101) and Up2 (102) represents cycle length CL (104), measured in block 37, from which heart rate can be determined, and the time between Pu2 and Dn marking the onset and the end of left ventricular ejection, encompassing the duration of LVET (105), calculated in block 38. Reference blood pressure data for calibration is entered in calibration register (39). Of note is that said three landmark points can be advantageously measured in the present invention by a single sensor device, for example, a standard, readily available photoplethysmography pulse detector.

Since LVET is also modulated by heart rate, the necessary adjustments are made in order to obtain a rate-corrected value, LVETc (310).

Block 310 is the blood pressure processor, which compares the percentage change of prevailing LVETc with baseline LVETc to calculate prevailing systolic, diastolic and pulse pressures according to formulae below. Said processor interacts with block 317 to calculate and store blood pressure trends in block 315. Data from the device whether real time or stored can be retrieved, displayed (314) or transmitted (313) to other devices such as a PC, central monitoring unit, smartwatch or cell phone.

In brief, percentage changes of LVETc are used as surrogates of percent changes in systolic and pulse blood pressures, referenced to initial calibration values. Given the simplicity, effectiveness and efficiency of the invention, the apparatus may be used in wearable devices (such as a wrist smart watch or a smart ring), implantable rhythm control devices (such as pacemakers, defibrillators), automatic drug infusion pumps, portable diagnostic medical devices and intensive care unit monitors allowing beat-to-beat continuous monitoring of blood pressure, as an alternative to intermittent, cumbersome, cuff-based blood pressure monitors or using invasive methods.

Operation of the Device

The invention comprises a hardware device and software, which when executed several calculations are done to start tracking beat-to-beat blood pressure changes. Operation of the device involves an initial calibration followed by full operation of the beat-to-beat blood pressure monitoring.

Initial calibration includes determining a reference blood pressure and a reference LVETc.

Initial calibration blood pressures obtained with a conventional apparatus should be entered to a memory register (39), expressed in mmHg and which can be periodically updated. Simultaneously one or more prevailing LVETs should be measured, averaged, and rate-corrected as hereinafter explained. The heart rate (HR) is obtained from the measurement of the beat-to-beat cycle length (CL) 104 that is, the time in seconds between the upstroke of the preceding beat (Up1) 101 and the upstroke of prevailing beat (Up2) 102. The heart rate will be given as HR=60/CL with CL expressed in seconds and HR as beats per minute. In the example of the present invention, systolic pressure and pulse pressure were used. Diastolic blood pressure therefore results from subtracting PP from SBP. Pulse pressure was used as a more reliable predictor of diastolic pressure. Baseline LVET is automatically measured and rate-corrected simultaneously with calibration blood pressure input. Several blood pressures and LVETc values may need to be averaged to smooth-out error, especially in case of cardiac arrhythmias. Heart rate correction of LVET, also referred to as normalization, removes the known effect of heart rate on LVET. It can be accomplished several ways, but for simplicity, in the present invention LVET is normalized to a heart rate of 60 bpm and referred to as LVETc, using the following calculation: LVETc=LVET+1.5*(HR−60), where 1.5 is the slope of the relationship between heart rate and LVET according to published studies, HR is the prevailing heart rate and 60 is the target normalization heart rate. As explained above, normalization of LVET can be done for any heart rate other than 60 bpm, including 0 bpm. Resulting value of LVETc is also stored in a memory register as a calibration value, which can be periodically updated if necessary.

An additional advantage of the present invention is that the LVET measurement on a peripheral artery correlate very closely with LVET measured with a pressure catheter in the central aorta and LVET is the same, independently of the artery from which it is measured. These observations indicate that unlike intra-vascular pressure that varies with the position of the selected artery relative to the heart, LVET remains unchanged and better reflects changes in central blood pressure. An example of this phenomenon can be demonstrated by measuring blood pressure with any commercially available wrist-based devices: BP values will be higher when the wrist is down than when the wrist is elevated above heart level.

In the event that input signals from the pulse sensor (31) to the aforementioned electronic device for continuous blood pressure monitoring (318) is not of enough amplitude it is possible to include an electronic signal amplifier (32) and/or an analog/digital converter (33) to optimize the signal (C1).

The reference calibration blood pressure is entered through a second operative connection (C2), using a classical blood pressure apparatus (312). Notwithstanding the above, note that the pressures could be entered through plurality of means, such as an interface (316) coupled to the electronic device through the same C2 port. Said interface (316) could be a keyboard or touch screen, input through another device or even linked by a wireless connection.

In the present invention, percentage changes of LVETc are used to predict associated percentage changes in blood pressure, namely systolic and pulse pressures, by using the slope of the correlation of blood pressure changes vs. LVETc changes, as obtained by inventors in experimental study. Said slopes are stored in memory block (317) and further used to calculate changes in systolic and pulse pressures (318). In a simple configuration of the electronic device according the present invention, a single initial calibration measurement is performed, indicated as calibration blood pressure and calibration LVETc. Said calibration values are in a memory block, which for the case is referred to as regression equation block (317).

Figure 3:
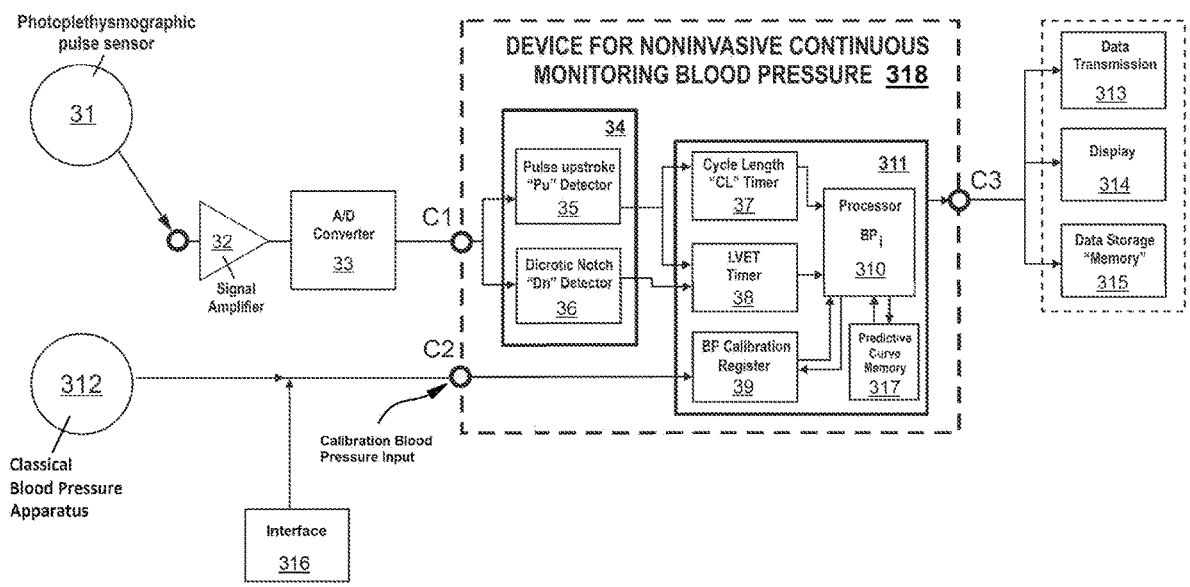
FIG. 3 shows a detailed block diagram of the electronic device based on the preferred embodiment of the invention.

Processor (310) is operationally connected to memory block (317) containing the systolic and pulse pressure regression slopes, and also is operationally coupled to the timers (37 and 38) and the register (39), and they can be considered part of a processing and storage unit (311) as illustrated in FIG. 3. Said processing and storage unit (311) may be provided with a third operating connection (C3) for connecting the electronic device for noninvasive continuous monitoring blood pressure (318) with a data transmission interface (313) a display or display means (314) or a memory for data storage (315).

Beat-to-Beat Blood Pressure Tracking

Once calibration values of systolic, diastolic and pulse pressures and LVETc are stored as explained above, subsequent beat-to-beat blood pressures can be calculated based on subsequent percentage changes of LVETc as compared to calibration BP values, using the equations shown below:

$$Systolic BP(SBP)=1.05*\% \text{ change LVETc+Calibration} SBP$$

$$Pulse\ Pressure(PP)=1.9*\% \text{ change LVETc+Calibration} PP$$

$$Diastolic\ blood\ pressure(DBP)=SBP-PP$$

Arterial pulse pressure was used instead of diastolic blood pressure because it had a better association with changes in LVETc. Above calculations can be done continuously beat-by-beat or periodically, and resulting values can be stored in memory. Display of said results can be numerical or as a trend, including heart rate, systolic and diastolic blood pressures.

What is claimed is:

1. An electronic device for a noninvasive beat-to-beat, continuous blood pressure monitoring in a subject using a left ventricular ejection time changes as surrogates of blood pressure changes, the device comprising:
   a first operative connection (C1) from where an arterial pulse signal (100) is input from a pulse sensor (31) for detecting a foot of an upstroke (101,102) and a dicrotic notch (103) of said arterial pulse signal;
   a cycle length timing and calculation circuitry (37) to measure a pulse cycle length, a heart rate, and a timing from the foot of the upstroke of said pulse signal to the dicrotic notch of said pulse signal to determine an interval (LVET (38)), and further calculate a rate-corrected left ventricular ejection time (LVETc);
   a second operative input (C2) to enter a calibration systolic, a diastolic, and pulse blood pressures from the subject simultaneously with the prevailing rate-corrected left ventricular ejection time (LVETc) of said arterial pulse for initial calibration;
   a third operating connection (C3) for connecting said electronic device for continuous, noninvasive blood pressure monitoring (318) with at least a transmission interface (313), a display, display device (314) and memory for data storage (315); and
   a processor (310) for the beat-by-beat calculation of the changes of values of arterial blood pressures as a function of changes of LVETc;
   wherein the values of prevailing systolic (SBP), the diastolic (DBP) and the pulse pressure (PP) are calculated as follows:

$$SBP=K1*\% \text{ change LVETc+Calibration}, PP=K2*\% \text{ change LVETc+Calibration} PP, DBP=SBP-PP;$$

wherein K1 is the slope of previously determined regression of LVETc changes vs. SBP changes, and K2 the slope of previously determined regression of LVETc vs PP; and
   wherein K2 is between 0.85 and 1.25 and K2, between 1.5 and 2.4.

2. The electronic device according to claim 1, wherein said prevailing blood pressures result from the following beat-by-beat calculations:

$$SBP=1.05*\% \text{ change LVETc+Calibration} SBP,$$
$$PP=1.9*\% \text{ change LVETc+Calibration} PP,$$
$$DBP=SBP-PP.$$

3. The electronic device according to claim 1, further comprising a photoplethysmography device for the detection of said arterial pulse signal.

4. The electronic device according to claim 1, further comprising an implantable arterial pulse detector to be embodied into an implantable device for continuous cardiac function monitoring.

5. The electronic device according to claim 1, wherein said prevailing blood pressure estimates are done using a difference rather than a percentage change of said rate-corrected left ventricular ejection time to predict prevailing blood pressure values.

* * * * *